(12) United States Patent
Otsubo et al.

(10) Patent No.: US 9,032,779 B2
(45) Date of Patent: May 19, 2015

(54) GAS SENSOR

(75) Inventors: Masanori Otsubo, Nagoya (JP); Takaya Yoshikawa, Kasugai (JP); Tomohiro Tajima, Kasugai (JP); Masao Tsuzuki, Kakamigahara (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 229 days.

(21) Appl. No.: 13/126,611

(22) PCT Filed: Oct. 20, 2009

(86) PCT No.: PCT/JP2009/005491
§ 371 (c)(1), (2), (4) Date: Apr. 28, 2011

(87) PCT Pub. No.: WO2010/050146
PCT Pub. Date: May 6, 2010

(65) Prior Publication Data
US 2011/0209523 A1   Sep. 1, 2011

(30) Foreign Application Priority Data
Oct. 29, 2008   (JP) ................ 2008-277566

(51) Int. Cl.
*G01N 7/00* (2006.01)
*G01N 27/407* (2006.01)
(52) U.S. Cl.
CPC ................ *G01N 27/4077* (2013.01)

(58) Field of Classification Search
CPC .................. G01N 27/407; G01N 33/0009
USPC ........................................... 73/23.31
See application file for complete search history.

(56) References Cited

U.S. PATENT DOCUMENTS

| | | | |
|---|---|---|---|
| 4,591,423 A * | 5/1986 | Kato et al. | 204/428 |
| 4,903,481 A | 2/1990 | Schuster et al. | |
| 5,447,618 A * | 9/1995 | Sugiyama et al. | 204/426 |
| 5,977,525 A | 11/1999 | Sahashi | |
| 6,346,179 B1 | 2/2002 | Makino et al. | |
| 6,348,141 B1 | 2/2002 | Kato et al. | |
| 6,849,238 B2 | 2/2005 | Weyl et al. | |
| 7,267,117 B2 | 9/2007 | Tonetti et al. | |
| 7,758,736 B2 * | 7/2010 | Okumura et al. | 204/428 |
| 2002/0150507 A1 | 10/2002 | Weyl et al. | |
| 2007/0215471 A1 | 9/2007 | Sakai et al. | |

FOREIGN PATENT DOCUMENTS

| | | | |
|---|---|---|---|
| EP | 0978721 A1 | 2/2000 | |
| EP | 1046906 A2 | 10/2000 | |

(Continued)

*Primary Examiner* — Laura Martin
*Assistant Examiner* — Alex Devito
(74) *Attorney, Agent, or Firm* — Sughrue Mion, PLLC (57) ABSTRACT

A gas sensor (1) has an inner protector (120) and an outer protector (110); the inner protector (120) has an inner wall portion (160) having an inner gas inlet (170) for introducing gas to be measured into the interior of the inner protector (120); the outer protector (110) has an outer wall portion (130) having an outer gas inlet (140) for introducing the gas to be measured into the interior of the outer protector (110); a clearance of 1.35 mm or less is provided between the detection portion (11) and at least a portion of the inner wall portion (160); and when the gas sensor (1) is in use, the inner protector (120) is higher in temperature than the outer protector (110).

8 Claims, 4 Drawing Sheets

(56) References Cited

FOREIGN PATENT DOCUMENTS

| | | |
|---|---|---|
| EP | 1918699 A1 | 5/2008 |
| JP | 1-167432 A | 7/1989 |
| JP | 3-2256 U | 1/1991 |
| JP | 9-184822 A | 7/1997 |
| JP | 10-170473 A | 6/1998 |
| JP | 10-293113 A | 11/1998 |
| JP | 11-2153 A | 1/1999 |
| JP | 2000-105215 A | 4/2000 |
| JP | 2000-171430 A | 6/2000 |
| JP | 2000-304719 A | 11/2000 |
| JP | 2002-181770 A | 6/2002 |
| JP | 2002-349371 A | 12/2002 |
| JP | 2005-61420 A | 3/2005 |
| JP | 2006-2761 A | 1/2006 |
| JP | 2007-279019 A | 10/2007 |
| JP | 2008-116355 A | 5/2008 |
| JP | 2009-80100 A | 4/2009 |

* cited by examiner

GAS SENSOR

TECHNICAL FIELD

The present invention relates to a gas sensor to be disposed in an intake passage, such as an intake gas passage through which intake gas supplied from the outside flows to an internal combustion engine, or an intake recirculation gas passage through which intake recirculation gas (recirculated exhaust gas) flows for reducing contaminant emission from the internal combustion engine.

BACKGROUND ART

Conventionally, in order to detect the oxygen concentration of intake gas (the air) supplied from the outside to an internal combustion engine, the following technique is employed: a gas sensor is disposed in an intake gas passage of the internal combustion engine, and the detected oxygen concentration is used in operation control of the internal combustion engine, thereby improving accuracy in air-fuel-ratio control of the internal combustion engine (refer to, for example, Patent Document 1).

Also, in recent years, for the purpose of reducing nitrogen oxides ($NO_x$) emitted from the internal combustion engine, a technique for reintroducing exhaust gas into an intake system (hereinafter, referred to as an exhaust gas recirculation system or an EGR system) is known (refer to, for example, Patent Document 2). In order to detect the oxygen concentration of intake recirculation gas, which is a mixture of exhaust gas from the EGR system and intake gas, disposing a gas sensor in an intake recirculation gas passage is known.

A known gas sensor to be installed in an intake passage, such as the intake gas passage or the intake recirculation gas passage, has a detection element in which electromotive force of different magnitude is generated or whose resistance varies, according to the concentration of, for example, $NO_x$ (nitrogen oxides) or oxygen (refer to, for example, Patent Document 3). While the gas sensor is exposed to a high-temperature gas to be measured, such as intake gas or intake recirculation gas, water contained in the gas adheres thereto (adhesion of water). Thus, the detection element is subjected to thermal shock and may be cracked. In order to cope with the problem, the gas sensor has a protector which covers the detection element, for protecting the detection element from adhesion of water. Further, although gas flowing through the intake passage contains much soot (carbon), the protector can prevent adhesion of soot to the detection element, thereby preventing deterioration in detection accuracy of the detection element.

The protector is provided in such a manner as to enclose a detection portion of the detection element for protecting the detection element from adhesion of water and soot. Meanwhile, in order to expose intake gas to the detection portion of the detection element, the protector has a gas inlet hole.

PRIOR ART DOCUMENTS

Patent Documents

Patent Document 1: Japanese Patent Application Laid-Open (kokai) No. 2005-61420
Patent Document 2: Japanese Patent Application Laid-Open (kokai) No. 2006-2761
Patent Document 3: Japanese Patent Application Laid-Open (kokai) No. H10-293113

SUMMARY OF THE INVENTION

Problems to be Solved by the Invention

However, when the gas inlet hole of the protector is relatively small, the gas inlet hole is clogged with soot (hereinafter, may be referred to as clogging). As a result, gas to be measured is not exposed to the detection portion of the detection element, resulting in deterioration in detection accuracy of the detection element. By contrast, when, with clogging of the protector taken into consideration, the gas inlet hole is relatively increased in size, the detection element suffers from adhesion of water or soot. As a result, the detection element may be cracked, or detection accuracy may deteriorate.

The present invention has been conceived to solve the above problem, and an object of the invention is to provide a gas sensor having a protector which is designed to restrain clogging of a gas inlet hole thereof and restrains adhesion of water and soot to a detection element.

Means for Solving the Problems

To achieve the above object, a gas sensor of configuration 1 comprises a plate-like detection element extending in a direction of an axis, having a detection portion in a front end region thereof for detecting a particular gas component contained in gas to be measured, and having a heater laminated thereon for heating the detection portion; a tubular metallic shell surrounding the detection element from radially outside of the detection element while allowing the detection portion to project from a front end thereof; and a protector accommodating therein the detection portion of the detection element and fixed to the metallic shell. The gas sensor is disposed in an intake passage of an internal combustion engine. The gas sensor is characterized in that the protector has an inner protector disposed with a gap existing between the detection portion and the inner protector, and an outer protector disposed with a gap existing between the inner protector and the outer protector; the inner protector has an inner wall portion disposed radially outward of the detection portion and having an inner gas inlet for introducing the gas to be measured into the interior of the inner protector; the outer protector has an outer wall portion disposed radially outward of the inner wall portion and having an outer gas inlet for introducing the gas to be measured into the interior of the outer protector; a clearance of 1.35 mm or less is provided between the detection portion and at least a portion of the inner wall portion; and when the gas sensor is in use, the inner protector is higher in temperature than the outer protector.

Also, a gas sensor of configuration 2 is characterized in that, in addition to having the above configuration 1, the inner wall portion and the detection portion form a clearance of 1.35 mm or less therebetween as measured over the entire region of the inner wall portion.

Further, a gas sensor of configuration 3 is characterized in that, in addition to having the above configuration 1 or 2, the outer wall portion and the inner wall portion form a clearance of 1 mm or greater therebetween as measured over the entire region of the outer wall portion.

Further, a gas sensor of configuration 4 is characterized in that, in addition to having any one of the above configurations 1 to 3, the outer gas inlet and the inner gas inlet do not overlap each other.

Further, a gas sensor of configuration 5 is characterized in that, in addition to having any one of the above configurations 1 to 4, the outer gas inlet is disposed toward a downstream side of the intake passage.

Further, a gas sensor of configuration 6 is characterized in that, in addition to having the above configuration 5, the outer protector has an outer bottom portion connected to a front end of the outer wall portion and the outer bottom portion has a gas outlet disposed toward an upstream side of the intake passage and adapted to allow the gas to be measured to flow out from the interior of the outer protector.

Further, a gas sensor of configuration 7 is characterized in that, in addition to having the above configuration 6, the inner protector has an inner bottom portion connected to a front end of the inner wall portion and covering at least a portion of a front end surface of the detection element.

Further, a gas sensor of configuration 8 is characterized in that, in addition to having any one of the above configurations 5 to 7, the inner gas inlet is disposed toward the upstream side of the intake passage.

Further, a gas sensor of configuration 9 is characterized in that, in addition to having the above configuration 8, the inner gas inlet is formed in such a manner as to expose at least one of side surfaces of the detection element.

Further, a gas sensor of configuration 10 is characterized in that, in addition to having the above configuration 8 or 9, the inner gas inlet is formed in such a manner as to expose at least a portion of a gas communication portion adapted to expose the gas to be measured to the detection portion.

Further, a gas sensor of configuration 11 is characterized in that, in addition to having the above configuration 9 or 10, the heater is disposed on a side toward the inner wall portion with respect to an axis of the detection element.

Effects of the Invention

The gas sensor of an invention according to configuration 1 comprises the protector having the inner protector and the outer protector. Thus, even when, with clogging of the outer gas inlet taken into consideration, the outer gas inlet is relatively increased in size, water and soot adhere to the inner wall portion of the inner protector, whereby adhesion of water and soot to the detection element can be restrained. As a result, the generation of cracking in the detection element can be restrained, and a deterioration in detection accuracy can be restrained.

Further, preferably, the temperature of the inner protector is 280° C. or higher. By virtue of this, water adhering to the inner wall portion can be positively evaporated, and soot can be positively removed from the inner wall portion. As a result, water and soot which once adhere to the inner wall portion can be prevented from being again contained in the gas to be measured which is to be introduced toward the detection element through the inner gas inlet, whereby adhesion of water and soot to the detection element can be restrained.

Meanwhile, according to the present invention, in order for the inner protector to have a temperature of 280° C. or higher, the inner protector is configured to receive heat from the heater adapted to heat the detection portion. This eliminates the need to separately provide heating means for heating the inner protector, thereby simplifying configuration.

In this case, when the gas sensor is in use, the temperature of the inner protector is rendered higher than that of the outer protector. This makes the outer protector less likely to receive heat from the heater, whereby the inner protector can efficiently have a temperature of 280° C. or higher. Accordingly, water adhering to the inner wall portion can be evaporated, and soot adhering to the inner wall portion can be burned or removed from the inner wall portion. As a result, adhesion of water and soot to the detection element can be restrained.

Specifically, the inner protector (inner wall portion) and the detection portion are disposed with a gap existing therebetween and such that a clearance of 1.35 mm or less is provided between the detection portion and at least a portion of the inner wall portion. By virtue of this, the inner protector has a temperature of 280° C. or higher through reception of heat from the heater laminated on the detection element and becomes higher in temperature than the outer protector. When the inner protector (inner wall portion) and the detection portion are in contact with each other, heat of the heater is conducted excessively to the inner protector; consequently, additional heater power is required for maintaining the detection portion at a predetermined temperature. Meanwhile, when the clearance between the inner wall portion and the detection portion is in excess of 1.35 mm, the inner protector is less likely to receive heat from the heater, so that difficulty is encountered in increasing the temperature of the inner protector.

The expression "when the gas sensor is in use, the inner protector is higher in temperature than the outer protector" means the following: when the gas sensor installed in the intake passage is detecting a particular gas component contained in gas to be measured, a temperature at any point on the inner protector is higher than a temperature at any point on the outer protector; and at the normal temperature, the inner protector and the outer protector may have the same temperature.

Even when the temperature of the outer protector is equal to or lower than that of the inner protector and equal to or higher than 280° C., water adhering to the outer wall portion can be positively evaporated, and soot can be positively burned or removed; however, the temperature of the outer protector may be 280° C. or lower.

The expression "a clearance of 1.35 mm or less is provided between the detection portion and at least a portion of the inner wall portion" means that the clearance between the detection portion and the inner wall portion may be 1.35 mm or less as measured at one or more points.

Further, a material used to form the inner protector may be higher in thermal conductivity than that used to form the outer protector. Through such selection of material, the temperature of the inner protector can be effectively rendered higher than that of the outer protector.

The temperature of the inner protector and that of the outer protector can be measured by use of a thermocouple or a radiation thermometer.

Further, in the gas sensor of an invention according to configuration 2, preferably, the inner wall portion and the detection portion form a clearance of 1.35 mm or less therebetween as measured over the entire region of the inner wall portion. By virtue of this, the inner protector can reliably receive heat from the heater.

Further, in the gas sensor of an invention according to configuration 3, preferably, the outer wall portion and the inner wall portion form a clearance of 1 mm or greater therebetween as measured over the entire region of the outer wall portion. By virtue of this, even when a large amount of water and soot is introduced into the gap between the inner wall portion and the outer wall portion, no clogging arises in the gap, and gas to be measured is sufficiently exposed to the detection portion of the detection element, whereby a deterioration in detection accuracy of the detection element can be restrained.

Further, in the gas sensor of an invention according to configuration 4, preferably, the outer gas inlet and the inner gas inlet do not overlap each other. By virtue of this, the gas to be measured which has passed through the outer gas inlet does not pass directly through the inner gas inlet, but inevitably comes into contact with the inner wall portion; thus, water and soot are apt to adhere to the inner wall portion of the inner protector. Therefore, the generation of cracking in the detection element can be restrained, and a deterioration in detection accuracy can be restrained.

The expression "the outer gas inlet and the inner gas inlet do not overlap each other" means that, when the outer gas inlet is viewed on an imaginary line which passes through the axis and is perpendicular to the axis, from a direction perpendicular to the axis, the inner gas inlet is invisible.

The configuration in which the outer gas inlet and the inner gas inlet do not overlap each other may be such that the inner gas inlet and the outer gas inlet are offset from each other in the axial direction or in the circumferential direction of the protector.

Further, in the gas sensor of an invention according to configuration 5, preferably, the outer gas inlet is disposed toward a downstream side of the intake passage. When the outer gas inlet is disposed toward the downstream side of the intake passage, gas to be measured is introduced into the interior of the outer protector from the downstream side of the intake passage while being swirled. By contrast, water and soot contained in the gas to be measured flow from the upstream side to the downstream side of the intake passage according to a flow of the gas to be measured which flows through the intake passage from the upstream side to the downstream side, and thus encounter difficulty in flowing through the intake passage from the downstream side to the upstream side and are thus unlikely to be introduced into the interior of the outer protector. Therefore, water and soot to be introduced into the interior of the outer protector can be reduced.

The expression "the outer gas inlet is disposed toward a downstream side of the intake passage" means that, when the gas sensor disposed in the intake passage is viewed from the downstream side of the intake passage, the outer gas inlet is visible.

Further, in the gas sensor of an invention according to configuration 6, the outer protector has an outer bottom portion connected to a front end of the outer wall portion, and the outer bottom portion may have a gas outlet disposed toward an upstream side of the intake passage and adapted to allow gas to be measured to flow out from the interior of the outer protector. Through provision of the gas outlet, the gas to be measured flows within the outer protector from the downstream side to the upstream side of the intake passage, whereby the gas to be measured can be efficiently renewed within the outer protector, thereby improving the detection accuracy of the detection portion in measurement of the gas to be measured.

Further, in the gas sensor of an invention according to configuration 7, preferably, the inner protector has an inner bottom portion connected to a front end of the inner wall portion and covering at least a portion of a front end surface of the detection element. By virtue of this, even when water and soot enter the interior of the outer protector through the gas outlet provided in the outer bottom portion, the water and soot adhere to the inner bottom portion, whereby adhesion of water and soot to the detection element can be restrained.

Further, in the gas sensor of an invention according to configuration 8, preferably, the inner gas inlet is disposed toward the upstream side of the intake passage. By virtue of this, the distance between the inner gas inlet and the outer gas inlet, which is disposed toward the downstream side of the intake passage, can be increased. Thus, the gas to be measured which has passed through the outer gas inlet is in contact with the inner wall portion of the inner protector over a longer range, whereby the amount of water and soot adhering to the inner wall portion can be increased.

The expression "the inner gas inlet is disposed toward the upstream side of the intake passage" means that, when the gas sensor is viewed from the upstream side of the intake passage, the inner gas inlet is disposed at a portion of the inner wall portion which faces a visible portion of the outer wall portion.

Further, in the gas sensor of an invention according to configuration 9, preferably, the inner gas inlet is formed in such a manner as to expose at least one of side surfaces of the detection element. By virtue of this, the gas to be measured is introduced in an increased amount into the interior of the inner protector. Thus, the gas to be measured becomes more likely to be exposed to the detection portion, thereby improving the detection accuracy of the detection portion in measurement of the gas to be measured.

Further, in the gas sensor of an invention according to configuration 10, preferably, the inner gas inlet is formed in such a manner as to expose at least a portion of a gas communication portion adapted to expose the gas to be measured to the detection portion. By virtue of this, the gas to be measured which has been introduced into the interior of the outer protector is exposed in an increased amount to the detection portion, thereby further improving the detection accuracy of the detection portion in measurement of the gas to be measured.

Further, in the gas sensor of an invention according to configuration 11, preferably, the heater is disposed on a side toward the inner wall portion with respect to an axis of the detection element. By virtue of this, heat from the heater can be efficiently transmitted to the inner protector. The expression "the heater is disposed on a side toward the inner wall portion with respect to an axis of the detection element" means that the distance between the inner wall portion and the heater is shorter than that between the inner wall portion and the axis of the detection element.

MODES FOR CARRYING OUT THE INVENTION

Figure 1:
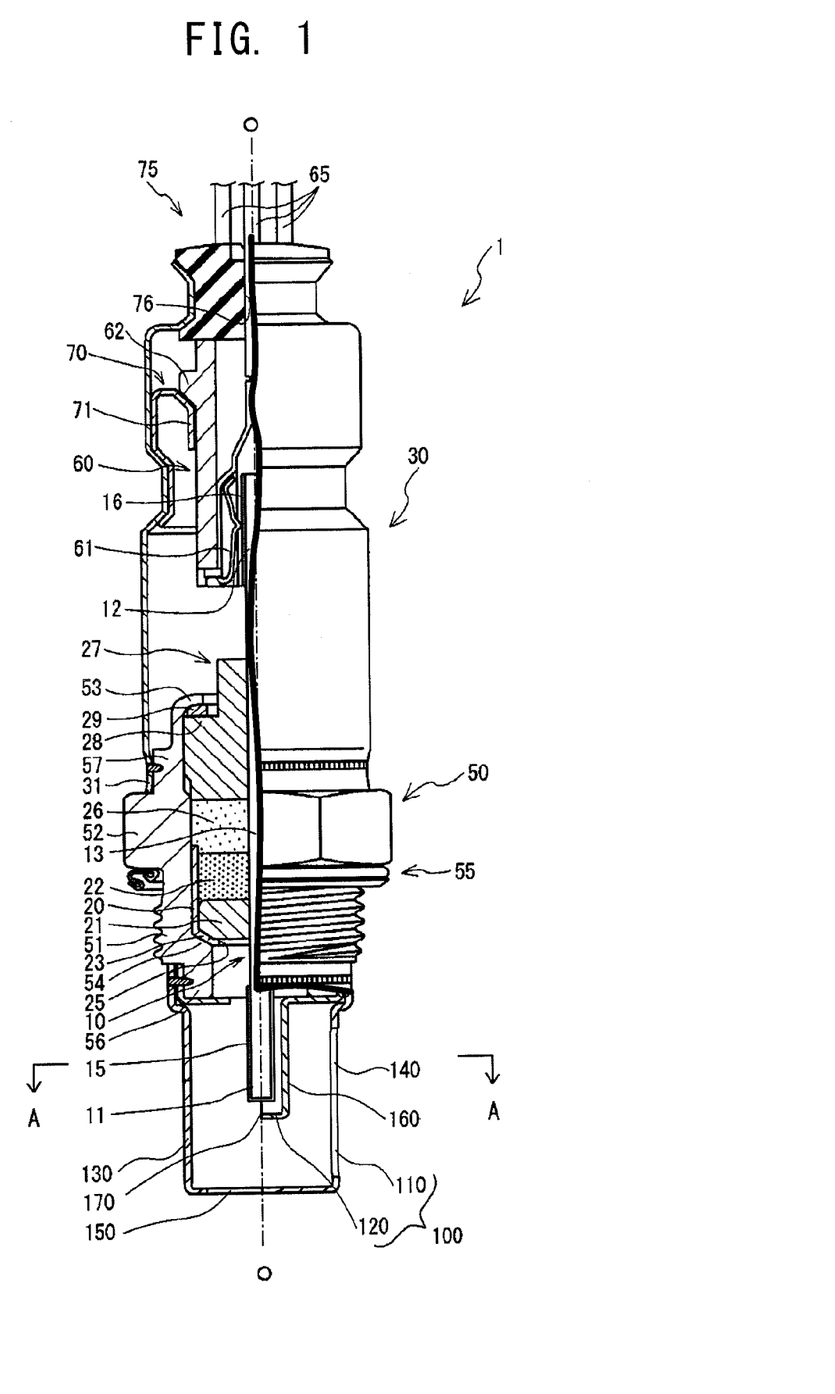
FIG. 1 Partially sectional view of a gas sensor 1 according to an embodiment of the present invention.

A gas sensor according to an embodiment of the present invention will next be described with reference to the drawings. First, the structure of a gas sensor 1 will be described, by way of example, with reference to FIG. 1. FIG. 1 is a partially sectional view of the gas sensor 1. In FIG. 1, the direction of an axis O (represented by a dash-dot line) of the gas sensor 1 coincides with the vertical direction. In the following description, a side toward a detection portion 11 of a detection element 10 held in the interior of the gas sensor 1 is referred to as a front side of the gas sensor 1, and a side toward a rear end portion 12 is referred to as a rear side of the gas sensor 1.

The gas sensor 1 shown in FIG. 1 is attached to an intake passage 2 (see FIG. 5) of an internal combustion engine. The detection portion 11 of the detection element 10 held in the interior of the gas sensor 1 is exposed to intake gas or intake recirculation gas which flows through the intake passage 2, for detecting an air/fuel ratio from the oxygen concentration of the intake gas or intake recirculation gas; i.e., the gas sensor 1 is a so-called full-range air/fuel ratio sensor.

The detection element 10 assumes the form of a strip extending in the direction of the axis O and is a substantially rectangular columnar laminate in which an element body 300 (see FIG. 2) for detecting an oxygen concentration and a heater 200 (see FIG. 2) for promptly activating the element body through application of heat are bonded together. In order to protect detection electrodes from poisoning by intake gas or intake recirculation gas, the detection portion 11 formed at the front end of the detection element 10 is covered with a protection layer 15. The rear end portion 12 of the detection element 10 has five electrode pads 16 (one of which is shown in FIG. 1) for allowing external connection with electrodes extending from the gas-sensing section and from the heater section.

Figure 2:
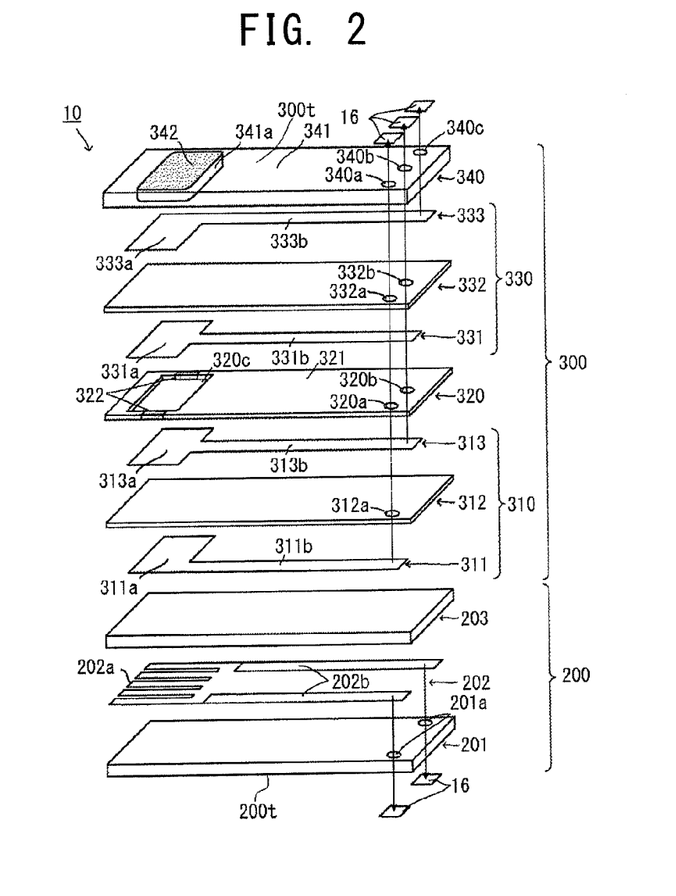
FIG. 2 Exploded perspective view of a detection element 10 of the embodiment.

FIG. 2 is an exploded perspective view of the detection element 10. Notably, FIG. 2 does not show the protection layer 15. As shown in FIG. 2, the detection element 10 is configured such that the element body 300 and the heater 200 are laminated together; further, the element body 300 is configured such that an oxygen concentration detection cell 310 and an oxygen pump cell 330 are laminated together.

The heater 200 has a first substrate 201 and a second substrate 203, which predominantly contain alumina, and a heat-generating element 202, which is sandwiched between the first substrate 201 and the second substrate 203 and predominantly contains platinum. The heat-generating element 202 has a heat-generating portion 202a located at the front end thereof, and a pair of heater lead portions 202b extending from the heat-generating portion 202a along the longitudinal direction of the first substrate 201. The ends of the heater lead portions 202b are electrically connected to corresponding electrode pads 16 via heater-side through holes 201a provided in the first substrate 201.

The oxygen concentration detection cell 310 includes a first solid electrolyte body 312, and a first electrode 311 and a second electrode 313, which are formed on respective opposite sides of the first solid electrolyte body 312. The first electrode 311 includes a first electrode portion 311a and a first lead portion 311b extending from the first electrode portion 311a along the longitudinal direction of the first solid electrolyte body 312. The second electrode 313 includes a second electrode portion 313a and a second lead portion 313b extending from the second electrode portion 313a along the longitudinal direction of the first solid electrolyte body 312.

The end of the first lead portion 311b is electrically connected to the corresponding electrode pad 16 via a first through hole 312a provided in the first solid electrolyte body 312, a second through hole 320a provided in an insulation layer 320 to be described later, a fourth through hole 332a provided in a second solid electrolyte body 332, and a sixth through hole 340a provided in an electrode protection layer 340. The end of the second lead portion 313b is electrically connected to the corresponding electrode pad 16 via a third through hole 320b provided in the insulation layer 320, a fifth through hole 332b provided in the second solid electrolyte body 332, and a seventh through hole 340b provided in the electrode protection layer 340.

Meanwhile, the oxygen pump cell 330 includes the second solid electrolyte body 332, and a third electrode 331 and a fourth electrode 333, which are formed on respective opposite sides of the second solid electrolyte body 332. The third electrode 331 includes a third electrode portion 331a and a third lead portion 331b extending from the third electrode portion 331a along the longitudinal direction of the second solid electrolyte body 332. The fourth electrode 333 includes a fourth electrode portion 333a and a fourth lead portion 333b extending from the fourth electrode portion 333a along the longitudinal direction of the second solid electrolyte body 332.

The end of the third lead portion 331b is electrically connected to the corresponding electrode pad 16 via the fifth through hole 332b provided in the second solid electrolyte body 332 and the seventh through hole 340b provided in the electrode protection layer 340. Meanwhile, the end of the fourth lead portion 333b is electrically connected to the corresponding electrode pad 16 via an eighth through hole 340c provided in the electrode protection layer 340. The second lead portion 313b and the third lead portion 331b have the same electric potential via the third through hole 320b.

The first solid electrolyte body 312 and the second solid electrolyte body 332 are partially-stabilized-zirconia sintered bodies which are formed by adding yttria ($Y_2O_3$) or calcia (CaO) serving as a stabilizer to zirconia ($ZrO_2$).

The heat-generating element 202, the first electrode 311, the second electrode 313, the third electrode 331, the fourth electrode 333, the electrode pads 16 can be formed from a platinum group element. Platinum group elements which are preferred for forming these components include Pt, Rh, and Pd. These elements can be used singly or in combination. Further, preferably, the heat-generating element 202, the first electrode 311, the second electrode 313, the third electrode 331, the fourth electrode 333, and the electrode pads 16 contain a ceramic component in addition to a main component of a platinum group element(s).

The insulation layer 320 is formed between the oxygen concentration detection cell 310 and the oxygen pump cell 330. The insulation layer 320 includes an insulation portion 321 and diffusion-controlling portions 322. A gas detection chamber 320c is formed in the insulation portion 321 of the insulation layer 320 at a position corresponding to the second electrode portion 313a and the third electrode portion 331a. The gas detection chamber 320c communicates with the ambient atmosphere along the lateral direction of the insulation layer 320. In the communication region of the insulation layer 320, the diffusion-controlling portions 322 are provided so as to establish gas diffusion at a predetermined flow rate between the ambient atmosphere and the gas detection chamber 320c. Notably, the diffusion-controlling portions 322 collectively correspond to the gas communication portion in the appended claims.

No particular limitation is imposed on the insulation portion 321, so long as the insulation portion 321 is of an electrically insulative ceramic sintered body. Examples of such a ceramic sintered body include oxide ceramics, such as alumina and mullite. The diffusion-controlling portions 322 are of a porous body of alumina. The diffusion-controlling portions 322 control the flow rate of gas to be detected when the gas flows into the gas detection chamber 320c.

The electrode protection layer 340 is formed on the surface of the second solid electrolyte body 332 such that the fourth electrode 333 is sandwiched therebetween. The electrode protection layer 340 is configured as follows: a porous electrode protection portion 342 which covers the fourth electrode portion 333a is fitted into a through hole 341a formed in a reinforcement portion 341 which covers the fourth lead portion 333b.

Referring back to FIG. 1, a closed-bottomed tubular metal cup 20 is disposed slightly frontward of the axial center of a trunk portion 13 of the detection element 10 in such a manner that the detection element 10 is inserted through the interior of the metal cup 20 with the detection portion 11 projecting from an opening 25 formed in the bottom of the metal cup 20. The metal cup 20 is a member for holding the detection element 10 in a metallic shell 50. A front-end peripheral-portion 23 located at a peripheral portion of the bottom of the metal cup 20 is tapered toward a tubular wall portion of the metal cup 20. The metal cup 20 contains a ceramic ring 21 made of alumina and a talc ring 22 formed by compacting a talc powder, in such a manner that the detection element 10 is inserted through the ceramic ring 21 and through the talc ring 22. The talc ring 22 is crushed within the metal cup 20 so as to tightly fill an associated space, thereby holding the detection element 10 in position in the metal cup 20.

An assembly of the metal cup 20 and the detection element 10 is surrounded by and held by the tubular metallic shell 50. The metallic shell 50 is adapted to fixedly attach the gas sensor 1 to the intake passage 2 of an automobile. The metallic shell 50 is formed from a low-carbon steel such as SUS430 and has an externally threaded portion 51 which is formed on an outer circumferential surface of the metallic shell 50 and located on a side toward the front end of the metallic shell 50. The metallic shell 50 has a front-end engagement portion 56 which is located frontward of the externally threaded portion 51 and engaged with a protector 100, which will be described later. The metallic shell 50 also has a tool engagement portion 52 which is formed at an axially central portion of the outer circumferential surface of the metallic shell 50 and with which a mounting tool is engaged. In order to prevent leakage of gas when the gas sensor 1 is attached to the intake passage 2, a gasket 55 is fitted to a portion of the metallic shell 50 between the front end face of the tool engagement portion 52 and the rear end of the externally threaded portion 51. The metallic shell 50 further has a rear-end engagement portion 57 which is located rearward of the tool engagement portion 52 and with which a sheath 30 to be described later is engaged, and a crimp portion 53 which is located rearward of the rear-end engagement portion 57 and adapted to crimp-hold the detection element 10 in the metallic shell 50.

The metallic shell 50 has a stepped portion 54 on its inner circumferential surface at a position substantially corresponding to the externally threaded portion 51. The front-end peripheral-portion 23 of the metal cup 20 which holds the detection element 10 is engaged with the stepped portion 54. Furthermore, a talc ring 26 is placed into the metallic shell 50 along the inner circumference of the metallic shell 50 toward the rear end of the metal cup 20 in such a state that the detection element 10 is inserted through the talc ring 26. A tubular sleeve 27 is fitted into the metallic shell 50 in such a manner as to press the talc ring 26 from the rear end of the talc ring 26. The sleeve 27 has a step-like shoulder portion 28 formed on the outer circumferential surface of a rear end portion of the sleeve 27. An annular crimp packing 29 is disposed on the shoulder portion 28. In this condition, the crimp portion 53 of the metallic shell 50 is crimped in such a manner as to press the shoulder portion 28 of the sleeve 27 frontward via the crimp packing 29. Being pressed by the sleeve 27, the talc ring 26 is crushed within the metallic shell 50, thereby tightly filling an associated space. By means of the talc ring 26 and the talc ring 22, which is previously placed in the metal cup 20, the metal cup 20 and the detection element 10 are held in position in the metallic shell 50. Gas tightness within the metallic shell 50 is maintained by means of the crimp packing 29 intervening between the crimp portion 53 and the shoulder portion 28 of the sleeve 27, thereby preventing outflow of combustion gas.

The rear end portion 12 of the detection element 10 projects rearward beyond the rear end (crimp portion 53) of the metallic shell 50. The rear end portion 12 is covered with a tubular separator 60 formed from an electrically insulative ceramic. The separator 60 internally holds the five electrode pads 16 formed on the rear end portion 12 of the detection element 10 and five connection terminals 61 (one of which is shown in FIG. 1), which are electrically connected to the respective electrode pads 16. Also, the separator 60 protectively accommodates connections between the connection terminals 61 and corresponding five lead wires 65 (three of which are shown in FIG. 1), which extend to the exterior of the gas sensor 1.

The tubular sheath 30 is disposed in such a manner as to surround the rear end portion 12 of the detection element 10 to which the separator 60 is fitted. The sheath 30 is made of stainless steel (e.g., SUS304). A front open end 31 of the sheath 30 is engaged with the outer circumference of the rear-end engagement portion 57 of the metallic shell 50. The open end 31 is crimped radially inward, and laser welding is performed on the open end 31 along the entire outer circumference of the open end 31, whereby the open end 31 is joined to the rear-end engagement portion 57. The sheath 30 and the metallic shell 50 are thus fixedly united together.

A tubular metal holder 70 is disposed in the gap between the sheath 30 and the separator 60. The metal holder 70 has a support portion 71, which is formed by inwardly bending a rear end of the metal holder 70. The separator 60 is inserted through the metal holder 70 such that a flange portion 62 formed on the outer circumference of a rear end portion of the separator 60 is engaged with the support portion 71, whereby the separator 60 is supported by the support portion 71. In this condition, a portion of the sheath 30 where the metal holder 70 is disposed is crimped radially inward, whereby the metal holder 70 which supports the separator 60 is fixed to the sheath 30.

A grommet 75 made of fluorine-containing rubber is fitted into a rear end opening of the sheath 30. The grommet 75 has five insertion holes 76 (one of which is shown in FIG. 1). The five lead wires 65 extending outwardly from the separator 60 are airtightly inserted through the respective insertion holes 76. In this condition, while the grommet 75 presses the separator 60 frontward, a portion of the sheath 30 which corresponds to the grommet 75 is crimped radially inward, whereby the grommet 75 is fixed to the rear end of the sheath 30.

Next, the protector 100, which is an essential member of the present invention, will be described.

Figure 3:
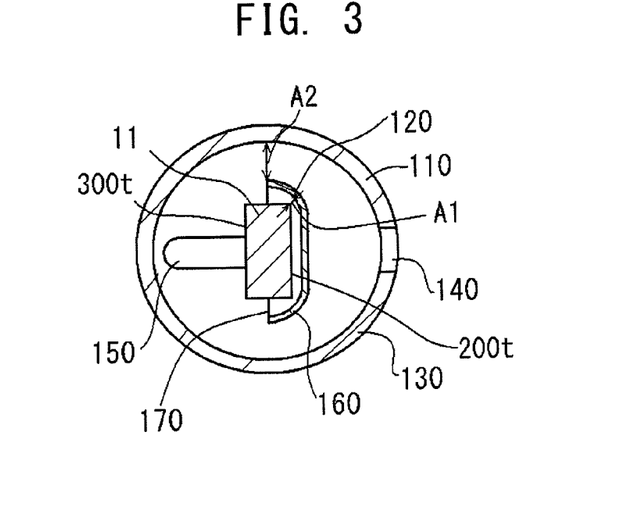
FIG. 3 Sectional view of the gas sensor 1 taken along line A-A of FIG. 1.
Figure 4:
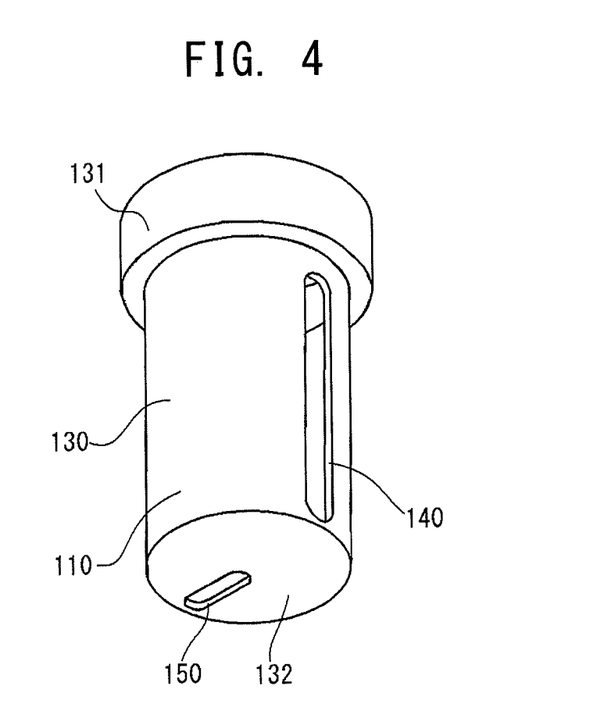
FIG. 4 Perspective view of an outer protector 110 of the embodiment.

The protector 100 is fixed to the front-end engagement portion 56 of the metallic shell 50 in such a manner as to enclose the detection portion 11 of the detection element 10. The protector 100 prevents adhesion, to the detection element 10, of soot and water contained in intake gas or intake recirculation gas. The structure of the protector 100 shown in FIG. 1 is described with reference to FIGS. 3 to 5. FIG. 3 is a sectional view taken along line A-A of FIG. 1; FIG. 4 is a perspective view of an outer protector 110; and FIG. 5 is a perspective view of an inner protector 120.

As shown in FIGS. 1 and 3, the protector 100 has such a dual structure as to have the inner protector 120 disposed with a gap existing between the detection portion 11 of the detection element 10 and the inner protector 120, and the outer protector 110 disposed with a gap existing between the inner protector 120 and the outer protector 110.

The outer protector 110 is formed from stainless steel, such as SUS304, and has, as shown in FIGS. 1 and 4, an outer wall portion 130 and an outer proximal end portion 131 greater in outside diameter than the outer wall portion 130. The outer proximal end portion 131 is engaged with the front-end engagement portion 56 of the metallic shell 50 and is laser-welded full circle to the metallic shell 50. Meanwhile, the outer wall portion 130 is located frontward of the outer proximal end portion 131, assumes a cylindrical form, and has a single slit-like outer gas inlet 140 formed therein and extending in the axial direction. Intake gas or intake recirculation gas is introduced from the outside into the outer protector 110 via the outer gas inlet 140. Further, the outer protector 110 has an outer bottom portion 132 provided at the front end of the outer wall portion 130. The outer bottom portion 132 has a gas outlet 150 through which intake gas or intake recirculation gas flows out. As will be described later, when the gas sensor 1 is disposed in the intake passage 2, the outer gas inlet 140 of the outer protector 110 is disposed toward the downstream side of the intake passage 2.

Figure 5:
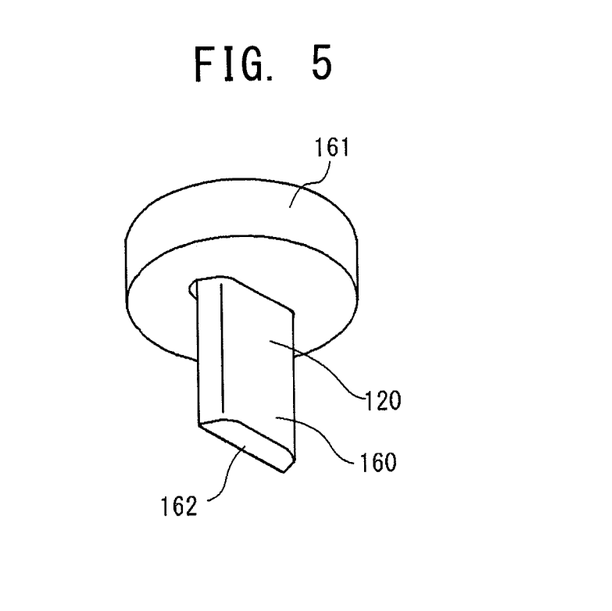
FIG. 5 Perspective view of an inner protector 120 of the embodiment.

Also, the inner protector 120 is formed from stainless steel, such as SUS304, and has, as shown in FIGS. 1 and 5, an inner wall portion 160 and an inner proximal end portion 161 greater in outside diameter than the inner wall portion 160. The inner proximal end portion 161 is engaged with the front-end engagement portion 56 of the metallic shell 50. The inner proximal end portion 161, together with the outer proximal end portion 131, is laser-welded full circle to the metallic shell 50. Further, the inner proximal end portion 161 is also welded to the front end surface of the front end engagement portion 56 of the metallic shell 50. Meanwhile, the inner wall portion 160 is provided frontward of the inner proximal end portion 161 in such an arcuately curved manner as to cover the heater 200 of the detection portion 11 of the detection element 10. The inner wall portion 160 has an inner gas inlet 170 at a radial end portion thereof. In the present embodiment, the element body 300 of the detection portion 11 projects from the inner gas inlet 170 and is exposed to the internal space of the outer protector 110. The inner protector 120 further has an inner bottom portion 162 provided at the front end of the inner wall portion 160 and covering the front end of the detection portion 11 of the detection element 10. As will be described later, when the gas sensor 1 is disposed in the intake passage 2, the inner gas inlet 170 of the inner protector 110 is disposed toward the upstream side of the intake passage 2.

Figure 6:
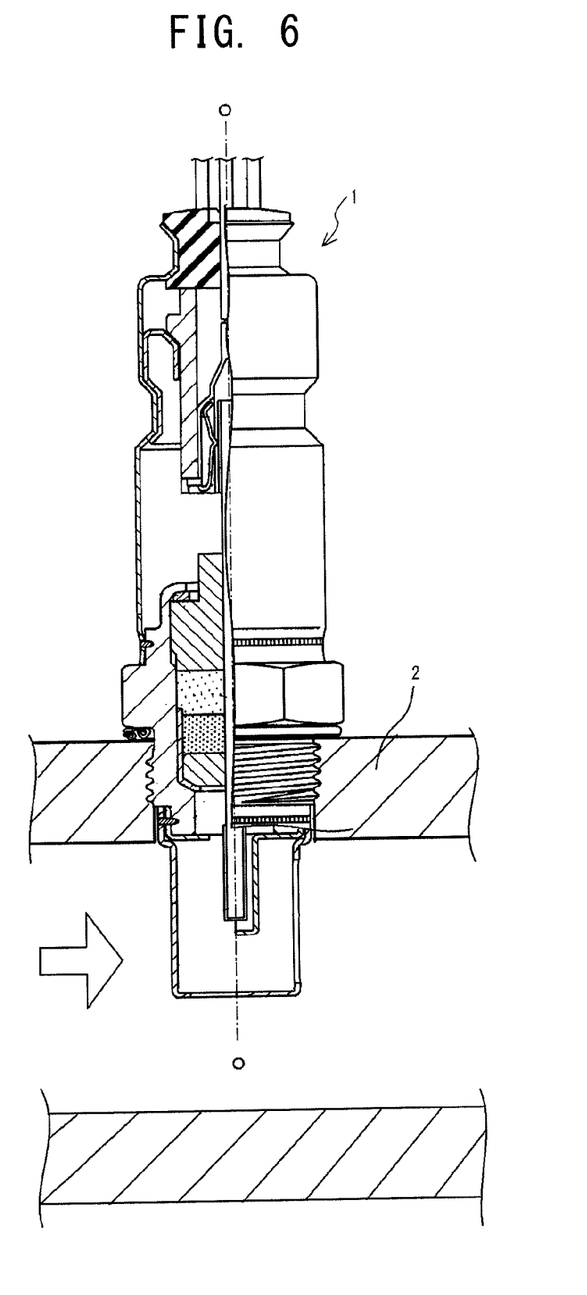
FIG. 6 View showing a state in which the gas sensor 1 of the embodiment is installed in an intake passage 2.

As shown in FIG. 6, the gas sensor 1 is disposed in the intake passage 2. Gas flows through the intake passage 2 from the upstream side to the downstream side (in the direction of the arrow of FIG. 6). At this time, the outer gas inlet 140 of the outer protector 110 is disposed toward the downstream side of the intake passage 2. By virtue of this, gas is introduced into the outer protector 110 from the downstream side of the intake passage 2 while being swirled.

By virtue of the protector 100 having the inner protector 120 and the outer protector 110, even when, with clogging of the outer gas inlet 140 taken into consideration, the outer gas inlet 140 is relatively increased in size, water and soot adhere to the inner wall portion 160 of the inner protector 120, whereby adhesion of water and soot to the detection element 10 can be restrained. As a result, the generation of cracking in the detection element 10 can be restrained, and a deterioration in detection accuracy can be restrained.

In the inner protector 120, the inner wall portion 160 and the detection portion 11 are disposed with a gap existing therebetween and such that a clearance A1 (see FIG. 3) between the inner wall portion 160 and the detection portion 11 is 0.5 mm. By virtue of the clearance A1 between the inner wall portion 160 and the detection portion 11 being 1.35 mm or less, when the gas sensor 1 detects a specific gas component contained in intake gas (when the gas sensor 1 is in use), the temperature of the inner protector 120 becomes higher than that of the outer protector 110. Specifically, the inner protector 120 has a temperature of 350° C., and the outer protector 110 has a temperature of 120° C. Thus, water adhering to the inner wall portion 160 can be evaporated, and soot adhering to the inner wall portion 160 can be burned or removed from the inner wall portion 160. As a result, water and soot which once adhere to the inner wall portion 160 can be prevented from being again contained in the gas which is to be introduced toward the detection element 10 through the inner gas inlet 170, whereby adhesion of water and soot to the detection element 10 can be restrained.

Also, the inner wall portion 160 is configured to receive heat from the heater 200 adapted to heat the detection portion 11. This eliminates the need to separately provide heating means for heating the inner protector 110, thereby simplifying configuration.

The temperature of the inner protector 120 and the clearance A1 between the detection portion 11 and the inner wall portion 160 of the inner protector 120 have the relation shown in Table 1 below. Table 1 plots the temperature of the inner protector 120 which was measured as follows: the detection portion 11 was disposed in the inner protector 120 (the outer protector 110 was not disposed), and the temperature was measured in a draft-free condition by a radiation thermometer one minute after the heater 200 was energized. As shown in Table 1, by means of the clearance A1 being 1.35 mm or less, the inner protector 120 can have a temperature of 280° C. or higher.

TABLE 1

Further, in the gas sensor 1, the outer wall portion 130 and the inner wall portion 160 form a clearance of 2.8 mm therebetween as measured over the entire region of the outer wall portion 130. By means of the clearance A2 between the outer wall portion 130 and the inner wall portion 160 being 1 mm or greater, even when a large amount of water and soot is introduced into the gap between the inner wall portion 160 and the outer wall portion 130, no clogging arises in the gap between the inner wall portion 160 and the outer wall portion 130, and gas to be measured is sufficiently exposed to the detection portion 11 of the detection element 10, whereby a deterioration in detection accuracy of the detection element 10 can be restrained.

When the outer protector 110 and the inner protector 120 are fixed to the front-end engagement portion 56 of the metallic shell 50, as shown in FIGS. 1 and 2, the outer gas inlet 140 and the inner gas inlet 170 are disposed in such a manner as not to overlap each other. By virtue of this, the gas which has passed through the outer gas inlet 140 does not pass directly through the inner gas inlet 170, but inevitably comes into contact with the inner wall portion 160; thus, water and soot are apt to adhere to the inner wall portion 160 of the inner protector 120. Therefore, the generation of cracking in the detection element 10 can be restrained, and a deterioration in detection accuracy can be restrained.

Further, the outer gas inlet 140 of the outer protector 110 is disposed toward the downstream side of the intake passage 2. By virtue of this, gas is introduced into the outer protector 110 from the downstream side of the intake passage 2 while being swirled. By contrast, water and soot contained in the gas flow from the upstream side to the downstream side of the intake passage according to a flow of the gas which flows through the intake passage 2 from the upstream side to the downstream side, and thus encounter difficulty in flowing through the intake passage 2 from the downstream side to the upstream side; thus, the water and soot are unlikely to be introduced into the interior of the outer protector 110. Therefore, water and soot to be introduced into the interior of the outer protector 110 can be reduced.

Further, the outer bottom portion 132 has the gas outlet 150 disposed toward the upstream side of the intake passage 2 and adapted to allow gas to be measured to flow out from the interior of the outer protector 110. Through provision of the gas outlet 150, the gas to be measured flows within the outer protector 110 from the downstream side to the upstream side of the intake passage 2, whereby the gas to be measured can be efficiently renewed within the outer protector 110, thereby improving the detection accuracy of the detection portion 11 in measurement of the gas to be measured.

Further, the inner protector 120 has the inner bottom portion 162 which covers the front end surface of the detection element 10. By virtue of this, even when water and soot enter the interior of the outer protector through the gas outlet 150 provided in the outer bottom portion 132, the water and soot adhere to the inner bottom portion 162, whereby adhesion of water and soot to the detection element can be restrained.

Also, the inner gas inlet 170 of the inner protector 110 is disposed toward the upstream side of the intake passage 2. By virtue of this, the distance between the inner gas inlet 170 and the outer gas inlet 140, which is disposed toward the downstream side of the intake passage 2, can be increased. Thus, the gas which has passed through the outer gas inlet 140 is in contact with the inner wall portion 160 of the inner protector 120 over a longer range until the gas reaches the inner gas inlet 170, whereby the amount of water and soot adhering to the inner wall portion 160 of the inner protector 120 can be increased.

Further, the inner gas inlet 170 is formed in such a manner as to expose a side surface 300t of the element body 300. By virtue of this, the gas to be measured is introduced in an increased amount into the interior of the inner protector 100. Thus, the gas to be measured becomes more likely to be exposed to the detection portion 11, thereby improving the detection accuracy of the detection portion 11 in measurement of the gas to be measured.

Further, the inner gas inlet 170 is formed in such a manner as to expose the diffusion-controlling portions 322. By virtue of this, the gas to be measured which has been introduced into the interior of the outer protector 110 is exposed in an increased amount to the detection portion 11, thereby further improving the detection accuracy of the detection portion 11 in measurement of the gas to be measured.

Further, the heater 200 is disposed on a side toward the inner wall portion 160 with respect to the axis of the detection element 10. That is, a side surface 200t of the heater 200 faces the inner wall portion 160, the side surface 200t partially constituting the detection element 10. By virtue of this, heat from the heater 200 can be efficiently transmitted to the inner protector 120.

The present invention is not limited to the above embodiment, but may be modified in various other forms. For example, in the present embodiment, a single outer gas inlet 140 and a single inner gas inlet 170 are provided in the outer wall portion 130 and the inner wall portion 160, respectively. However, the present invention is not limited thereto. A plurality of outer gas inlets and a plurality of inner gas inlets may be provided.

Also, in the present embodiment, the outer gas inlet 140 assumes the form of a slit extending in the axial direction. However, the present invention is not limited thereto. The outer gas inlet 140 may have a circular shape.

Also, in the present embodiment, the inner wall portion 160 is formed into an arcuately curved shape. However, the present invention is not limited thereto. The inner wall portion 160 may be formed into such a cylindrical shape as to cover most of the detection element 10 as in the case of the outer wall portion 130.

Also, in the present embodiment, the outer gas inlet 140 and the inner gas inlet 170 are formed toward the downstream side and the upstream side, respectively, of the intake passage. However, the present invention is not limited thereto. The outer gas inlet and the inner gas inlet may be formed toward the upstream side and the downstream side, respectively, of the intake passage.

The present embodiment is described while mentioning a full-range air/fuel ratio sensor. However, the present invention can be applied similarly to protectors to be attached to oxygen sensors, $NO_x$ sensors, HC sensors, temperature sensors, etc.

DESCRIPTION OF REFERENCE NUMERALS

1: gas sensor
10: detection element
11: detection portion
50: metallic shell
100: protector
110: outer protector
120: inner protector
130: outer wall portion
140: outer gas inlet
160: inner wall portion
170: inner gas inlet 200: heater
300: element body

The invention claimed is:

1. A gas sensor comprising:
a plate-like detection element extending in a direction of an axis, having a detection portion in a front end region thereof for detecting a particular gas component contained in gas to be measured, and having a heater laminated thereon for heating the detection portion;
a tubular metallic shell surrounding the detection element from radially outside of the detection element while allowing the detection portion to project from a front end thereof; and
a protector accommodating therein the detection portion of the detection element and fixed to the metallic shell;
the gas sensor being disposed in an intake passage of an internal combustion engine;
the gas sensor being characterized in that:
the protector has an inner protector disposed with a gap existing between the detection portion and the inner protector, and an outer protector disposed with a gap existing between the inner protector and the outer protector;
the inner protector has an inner wall portion disposed radially outward of the detection portion and having an inner gas inlet for introducing the gas to be measured into the interior of the inner protector;
the outer protector has an outer wall portion disposed radially outward of the inner wall portion and having an outer gas inlet for introducing the gas to be measured into the interior of the outer protector;
the outer gas inlet is disposed only toward a downstream side of the intake passage and the inner gas inlet is disposed only toward an upstream side of the intake passage, such that the gas to be measured traverses a circumference of the outer gas protector and enters the outer gas inlet on the downstream side of the intake passage and then traverses a circumference of the inner gas protector and enters the inner gas inlet on the upstream side of the intake passage,
wherein the outer wall portion has a half portion defined as half of a circumference of the outer wall portion, wherein the outer gas inlet is present only on the half portion of the outer wall portion that does not face the inner gas inlet, and the inner gas inlet does not face the outer gas inlet;
a clearance of 1.35 mm or less is provided between the detection portion and at least a portion of the inner wall portion;
when the gas sensor is in use, the inner protector is higher in temperature than the outer protector; and
the outer wall portion and the inner wall portion form a clearance of 1 mm or greater therebetween as measured over the entire region of the outer wall portion.

2. A gas sensor according to claim 1, wherein the inner wall portion and the detection portion form a clearance of 1.35 mm or less therebetween as measured over the entire region of the inner wall portion.

3. A gas sensor according to claim 1, wherein the outer gas inlet and the inner gas inlet do not overlap each other.

4. A gas sensor according to claim 1, wherein the outer protector has an outer bottom portion connected to a front end of the outer wall portion, and
the outer bottom portion has a gas outlet disposed toward an upstream side of the intake passage and adapted to allow the gas to be measured to flow out from the interior of the outer protector.

5. A gas sensor according to claim 4, wherein the inner protector has an inner bottom portion connected to a front end of the inner wall portion and covering at least a portion of a front end surface of the detection element.

6. A gas sensor according to claim 1, wherein the inner gas inlet is formed in such a manner as to expose at least one of side surfaces of the detection element.

7. A gas sensor according to claim 6, wherein the heater is disposed on a side toward the inner wall portion with respect to an axis of the detection element.

8. A gas sensor according to claim 1, wherein the inner gas inlet is formed in such a manner as to expose at least a portion of a gas communication portion adapted to expose the gas to be measured to the detection portion.

* * * * *